US00PP13317P2

(12) United States Plant Patent
Zary

(10) Patent No.: US PP13,317 P2
(45) Date of Patent: Dec. 3, 2002

(54) HYBRID TEA ROSE PLANT NAMED 'JACINBER'

(75) Inventor: Keith W. Zary, Thousand Oaks, CA (US)

(73) Assignee: Jackson & PErkins Wholesale, Inc., Medford, OR (US)

( * ) Notice: Subject to any disclaimer, the term of this patent is extended or adjusted under 35 U.S.C. 154(b) by 0 days.

(21) Appl. No.: 09/724,696

(22) Filed: Nov. 28, 2000

(51) Int. Cl.[7] ..... A01H 5/00
(52) U.S. Cl. ..... Plt./140
(58) Field of Search ..... Plt./140

*Primary Examiner*—Bruce R. Campell
*Assistant Examiner*—Susan B. McCormick
(74) *Attorney, Agent, or Firm*—Klarquist Sparkman, LLP

(57) ABSTRACT

Hybrid tea rose plant having bright red flowers having a lighter color on the reverse of the petals; dark reen, glossy foliage; high-centered buds; and long cutting stems.

1 Drawing Sheet

The present invention relates to a new and distinct variety of rose plant of the hybrid tea class which was originated by me by crossing POULman (U.S. Plant Pat. No. 6,264) with the variety JACpico (U.S. Plant Pat. No. 3,997).

The primary objective of this breeding was to produce a new rose variety having a high-centered flower form, large foliage and long buds of the female parent combined with the bright red flower color and glossy foliage of the male parent. The objective was substantially achieved, along with other desirable improvements, as evidenced by the following unique combination of characteristics that are outstanding in the new variety and that distinguish it from its parents, as well as from all other varieties of which I am aware:

1. Bright red flower;
2. Lighter in color on petal reverse;
3. Dark green, glossy foliage;
4. High-centered bud; and
5. Long cutting stems.

Asexual reproduction of this new variety by budding, as performed at Wasco, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart (1966), except where ordinary dictionary significance of color is indicated.

Parentage:

*Seed parent*.—JACpico (U.S. Plant Pat. No. 3,997).

*Pollen parent*.—POULman (U.S. Plant Pat. No. 6,264).

Classification:

*Botanical*.—*Rosa hybrida*.

*Commercial*.—Hybrid tea.

FLOWER

Observations made from specimens grown in a garden environment at Somis, Calif. at two years of age in January, 1999–August, 2000.

Blooming habit: Continuous.

Bud:

*Size*.—About 1¾ inches long and 4½ inches in diameter at the base when the petals start to unfurl.

*Form*.—The bud form is long, pointed ovoid.

*Color*.—When sepals first divide, bud color is Red Group 53B at the tip of the bud. The color changes down the petals to Red Group 53D with veins clearly evident. Often the mid-rib is also clearly evident as White Group 155D. Finally, the colorspot at the petal base is clearly visible. When half blown, the upper sides of the petals are Red Group 45A; and the lower sides of the petals are Red Group 53D.

*Sepals*.—Color: Green Group 138B. Length: 1½–1¾ inches. Width: ½–¾ inches. Surface texture: Covered in fine hairs. There are three normally to heavily appendaged sepals. There are two unappendaged sepals with hairy edges.

*Receptacle*.—Color: Green Group 137D, often with Greyed-Purple Group 183B in areas exposed to bright sunlight. Shape: Funnel. Size: Large, about 7/16 inch×½ inch. Surface: Smooth.

*Peduncle*.—Length: Short, averaging 2½ inches. Surface: Somewhat prickly. Color: Green Group 137B but usually Greyed-Purple Group 183B in areas exposed to bright sunlight. Strength: Stiff, erect and heavy.

Bloom:

*Size*.—Large. Average open size is 5½ inches.

*Borne*.—Singly.

*Stems*.—Strength: Strong. Average length is about 16"–18".

*Form*.—When first open: High centered. Permanence: Retains its form to the end, outer petals curl back with some quilling.

*Petalage*.—Number of petals under normal conditions: 45–50.

*Color*.—The upper sides of the petals are Red Group 45A. The reverse sides of the petals are Red Group 53D. The base of each petal has on the upper surface a distinct 5/16"×¼" Yellow Group 8C colorspot with a small area of Yellow Group 8A in the center. The lower surface colorspot is ½"×½" and White Group 155D with a small (1/16"×1/16") Yellow Group 2C point. The major color on the upper side is Red Group 45A.

*Variegations*.—There are white (White Group 155D) mid-ribs visible on the petal reverse. There are also occassional (White Group 155D) streaks on the interior upper surface petals.

*Discoloration*.—The general tonality at the end of the first day: No change. At the end of the third day: No change. By day 6, there is a general change in color to Red-Purple Group 57C. Petals drop by day 7.

*Fragrance*.—Moderate, mild fruity scent.

Petals:

*Texture*.—Thick, leathery.

*Shape*.—Round to deltoid.

*Base*.—Cuneate.

*Apex*.—Obtuse.

*Form*.—Tips slightly recurved, edges slightly quilled.

*Arrangement*.—Imbricated. There are no petaloids in the center.

*Persistence*.—Petals drop off cleanly before drying.

*Lastingness*.—On the plant: Fair (about 6–7 days). As a cut flower: Long (about 8–9 days).

Reproductive parts:

*Anthers*.—Size: 1/16–1/8 inch. Quantity: 100–120. Color: Yellow Group 11B. Arrangement: Regular around styles.

*Filaments*.—Color: Red-Purple Group 61C. Length: 3/16–1/4 inch.

*Pollen*.—Color: Yellow-Orange Group 22D.

*Pistils*.—Number: 80–100.

*Styles*.—Color: Red Group 53D. Length: 3/16–1/4 inch.

*Stigmas*.—Color: Orange-White Group 159B. Length: 1/16 inch.

*Hips*.—None observed.

Plant:

*Form*.—Bush.

*Growth*.—Very vigorous, upright and branching. At maturity (one year after planting), height is 6 feet, width is 4 feet.

Foliage: Number of leaflets on normal mid-stem leaves: 5 or 7.

*Size*.—Large (7 inches long×5 inches wide).

*Quantity*.—Abundant.

*Color*.—New foliage: Upper surface: Greyed-Purple Group 183C. Lower surface: Greyed-Purple Group 183C. Old foliage: Upper surface: Green Group 139A. Lower surface: Green Group 139C.

Leaflets:

*Size*.—Length: 1 5/8–2 3/8 inch. Width: 13/16–1 1/4 inch.

*Shape*.—Pointed oval.

*Texture*.—Leathery, glossy.

*Edge*.—Serrated.

*Serration*.—Single, small.

*Petiole rachis*.—Color: Greyed-Purple Group 183D (Upper); Yellow-Green Group 146D (Lower).

*Petiole underside*.—Smooth, with occassional prickles.

*Stipules*.—Long (about 1 inch), bearded, edged in glands.

*Disease resistance*.—Susceptible to mildew and black-spot; resistant to rust under normal growing conditions.

*Venation pattern*.—Costate.

*Vein color: lower surface*.—Green Group 139C.

Wood:

*New wood*.—Color: Greyed-Purple Group 183C. Bark: Smooth.

*Old wood*.—Color: Green Group 137C, but stays Greyed-Purple Group 183C for several weeks. Bark: Smooth.

Prickles:

*Quantity*.—On main canes from base: 14 thorns per six inch stem. On laterals from main canes: 14 thorns per six inch stem.

*Form*.—Medium, hooked downward.

*Color when young*.—Greyed-Purple Group 183C.

*Color when mature*.—Greyed-Orange Group 165A.

*Length*.—1/4 inch–3/8 inch.

Small prickles:

*Quantity*.—On main stalks: None. On laterals: None. There are a few small thorns on the peduncle and on the wood just below the peduncle.

*Color*.—Greyed-Purple Group 183C when young. Changes to Greyed-Red Group 183D and finally Greyed-Orange Group 165A when fully mature.

I claim:

1. A new and distinct variety of rose plant of the hybrid tea class, substantially as herein shown and described, characterized particularly by its bright red flowers having a lighter color on the reverse of the petals; dark green, glossy foliage; high-centered buds; and long cutting stems.

* * * * *

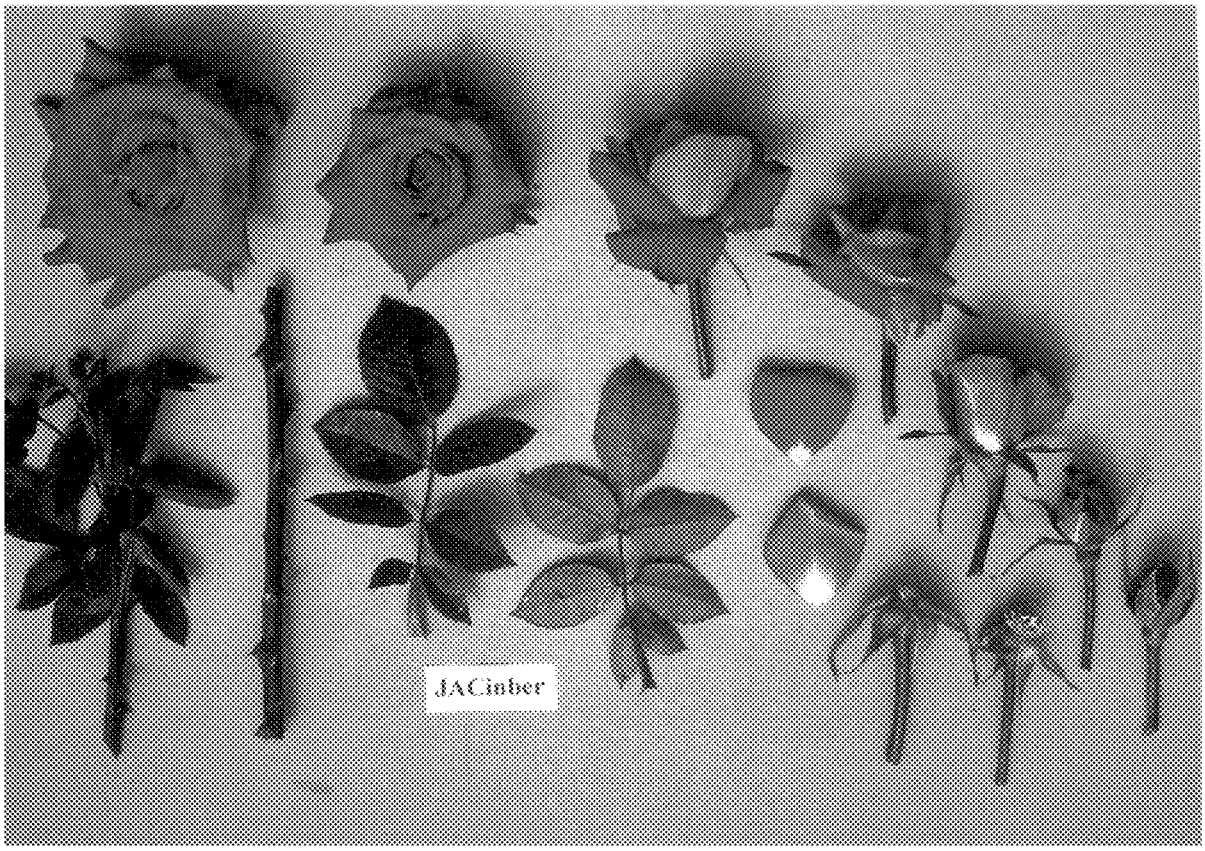
JACinber